US006423823B1

(12) United States Patent
neé Martini et al.

(10) Patent No.: US 6,423,823 B1
(45) Date of Patent: Jul. 23, 2002

(54) ORGANIC CHEMICAL COMPOUNDS AND METHOD FOR PRODUCING THE SAME

(75) Inventors: Ulrike Martini-Marr neé Martini, Heppenheim/Bergstrasse; Anke Mayer-Bartschmid neé Mayer, Velbert; Heidrun Anke, Kaiserslautern, all of (DE); Olov Sterner, Malmö (SE); Michael Kilian, Leverkusen (DE); Ulrike Wachendorff-Neumann, Neuwied (DE); Achim Harder, Köln (DE); Peter Jeschke, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/555,922

(22) PCT Filed: Nov. 25, 1998

(86) PCT No.: PCT/EP98/07611

§ 371 (c)(1),
(2), (4) Date: Nov. 28, 2000

(87) PCT Pub. No.: WO99/29714

PCT Pub. Date: Jun. 17, 1999

(30) Foreign Application Priority Data

Dec. 8, 1997 (DE) .......................................... 197 54 298

(51) Int. Cl.[7] .............................................. A61K 38/12
(52) U.S. Cl. ........................ 530/317; 530/327; 514/11; 514/14
(58) Field of Search ................................. 530/317, 327; 514/11, 14

(56) References Cited

FOREIGN PATENT DOCUMENTS

WO     97/20857     6/1997

OTHER PUBLICATIONS

Stephenson Drugs 60 (5) 985–95, 2000.*
Cutrona, Comprehensive Therapy, 20 (8) 445–58, 1994.*
Mandell Medical Clinics of North America 72 (3) 669–90, 1988.*
Buchel, Edwin et al, "Omphalotins B, C and D, nematicidal cyclopeptides from Omphalotus Olearius. Absolute configuration of omphalotin A", Tetrahedron (1998), 54(20), 5345–5352 May 1998, XP004116435.
Chemical Abstracts, vol. 126, No. 11, Mar. 17, 1997, Abstract No. 141834, A. Mayer et al.

* cited by examiner

Primary Examiner—Christopher S. F. Low
Assistant Examiner—David Lukton
(74) Attorney, Agent, or Firm—Joseph C. Gil; John E. Mrozinski, Jr.

(57) ABSTRACT

The present invention relates to novel organochemical compounds, referred to as omphalotins for short, a process for their preparation by an essentially microbiological route and their use as pesticides, preferably for controlling animal pests.

19 Claims, 1 Drawing Sheet

FIG. 1

ORGANIC CHEMICAL COMPOUNDS AND METHOD FOR PRODUCING THE SAME

FIELD OF THE INVENTION

The present invention relates to novel organochemical compounds, hereinafter referred to as omphalotins, a process for their preparation by an essentially microbiological route and their use as pesticides, preferably for controlling animal pests.

BACKGROUND OF THE INVENTION

One compound of the omphalotin class, which is referred to as omphalotin A below, has already been described in WO 97/20857.

DETAILED DESCRIPTION OF THE INVENTION

The novel omphalotins B, C and D have been found and, based on the present spectroscopic and other analytical data, the following formula (I) is proposed:

where and where $R^1$, $R^2$ and $R^3$ represent hydrogen or acyl.
Preferably,
$R^1$, $R^2$ and $R^3$ represent H, —CO—CH$_3$ or The invention also provides all stereoisomers resulting from combination of all possible (R) and (S) and, respectively (D) and (L) configurations of the asymmetrically substituted carbon atoms, and mixtures of these isomers.

Furthermore, it has been found that the novel omphalotins can be employed for controlling pests and parasites in plants and warm-blooded animals. In particular, they have high activity against nematodes and arthropods (like insects and arachnids). Owing to these properties, the novel compounds and compositions comprising these compounds can be employed particularly advantageously in crop protection, in the protection of stored products, in the hygiene sector and in animal breeding and animal husbandry.

The novel compounds of the formula (I) are obtained by cultivating suitable microorganisms from the class of the Basidiomycetes, preferably from the genera Omphalotus and Lampteromyces, particularly preferably Omphalotus, in a customary manner under aerobic conditions in a culture medium which contains assimilable carbon and nitrogen sources and mineral salts and isolating the desired compound by customary methods.

Knowing the properties of the novel compounds according to the invention, it is possible in an easy and quick manner to select the appropriate microorganism strains which produce the omphalotins according to the invention by routine processes, with the aid of customary chromatographic, spectroscopic, microbiological (for example inhibition zone test) and/or biological methods (for example by determining the activity against nematodes or insects).

For the microbiological preparation of the compounds according to the invention, preference is given to using omphalotus strains, in particular *Omphalotus olearius* strains. Very particular preference is given to using the *Omphalotus olearius* strains No. 83 039, 90 173, 91 050, 92 095, 93 162 and 90 170 and those variants and mutants of these strains which have features which are essential for carrying out the present invention, or which have the same function.

The strains can be described as follows:

1. Comparison of the morphology of the mycelium of various *Omphalotus olearius* strains on solid medium (M1)

| Fungus strain | Mycelium condition and colour |
|---|---|
| Omphalotus olearius 83 039 (DSM 9737) | The mycelium which is white at the beginning of growth only changes colour to a pale yellow, in rare cases somewhat brownish. Secretions, as observed with the other strains, were not observed. |
| Omphalotus olearius 90 170 (DSM 9742) | The young mycelium is white-fluffy, the older mycelium changes colour to orange-black. In some cases, droplets of brown colour are secreted. |
| Omphalotus olearius 90 173 (DSM 9738) | The young white mycelium grows less dense and fluffy than 90 170. The older mycelium is initially pale yellow and later changes colour to orange-black. In some cases, brown secretions are observed. |
| Omphalotus olearius 91 050 (DSM 9739) | Growth and mycelium colour are similar to that/those of 90 170, however, the secretions of brown droplets are more numerous. |
| Omphalotus olearius 92 095 (DSM 9740) | The young white mycelium changes colour to an intense orange, later slightly brownish. The secretion of brown droplets is very pronounced. The mycelium does not turn black. |
| Omphalotus olearius 93 162 (DSM 9741) | Similar to 92 095, the young yellow mycelium changes colour to an intense orange and likewise secretes many brown drops. |

2. Growth of various *Omphalotus olearius* strains at different temperatures in 1 l of a shaken culture M1 medium in a 2 l Erlenmeyer flask.

| | Incubation temperature [° C.] | | |
|---|---|---|---|
| Fungus strain | 24 | 27 | 30 |
| Omphalotus olearius 83 039 (DSM 9737) | maximum growth rate | medium growth rate | strongly reduced growth |
| Omphalotus olearius 90 170 (DSM 9742) | Slightly less growth than at 30° C. | | maximum growth rate |
| Omphalotus olearius 90 173 (DSM 9738) | Identical growth at all temperatures | | |
| Omphalotus olearius 91 050 (DSM 9739) | Identical growth at all temperatures | | |
| Omphalotus olearius 92 095 (DSM 9740) | medium growth rate | maximum growth rate | lowest growth rate |
| Omphalotus olearius 93 162 (DSM 9741) | maximum growth rate | maximum growth rate | lowest growth rate |

3. Form and size of the pellets of the various Omphalotus olearius strains during growth in liquid culture (M1)

| Fungus strain | Form and size of pellet |
|---|---|
| Omphalotus olearius 83 039 (DSM 9737) | The fungus forms solid pellets of a diameter of 0.5 to 1.5 cm |
| Omphalotus olearius 90 170 (DSM 9742) | The fungus grows in very small solid pellets having a diameter of about 0.5 cm |
| Omphalotus olearius 90 173 (DSM 9738) | The fungus grows with a similar pellet form and size as 90 170 |
| Omphalotus olearius 91 050 (DSM 9739) | The pellet size varies frequently but is generally slightly greater than for 90 170 (0.5 to 1.5 cm). The pellets are "frazzled". |
| Omphalotus olearius 92 095 (DSM 9740) | The fungus forms the largest pellets of a diameter of 1 to 2 cm and a "prickly" surface. |
| Omphalotus olearius 93 162 (DSM 9741) | The fungus forms pellets having a diameter of up to 1.5 cm and less solid, more "frazzled" structure. |

The abovementioned *Omphalotus olearius* strains have been deposited at the Deutsche Sammlung von Mikroorganismen und Zellkulturen GmbH (DSM), Mascheroder Weg 1b, D 38124 Braunschweig, Federal Republic of Germany, in accordance with the provisions of the Treaty of Budapest on the international recognition of the deposition of microorganisms for the purpose of patent processes and have the following deposition numbers or entry numbers:

| Strain | Deposition or entry number | Date of deposition |
|---|---|---|
| Omphalotus olearius No. 83 039 (syn. Omphalotus illudens) | DSM 9737 | 13.02.1995 |
| Omphalotus olearius No. 90 173 | DSM 9738 | 13.02.1995 |
| Omphalotus olearius No. 91 050 | DSM 9739 | 13.02.1995 |
| Omphalotus olearius No. 92 095 | DSM 9740 | 13.O2.1995 |
| Omphalotus olearius No. 93 162 | DSM 9741 | 13.02.1995 |
| Omphalotus olearius No. 90 170 | DSM 9742 | 13.02.1995 |

The structures of the omphalotins isolated from *Omphalotus olearius* were elucidated with the aid of $^1$H-, $^{13}$C-, COSY-, HMQC- and HMBC-NMR spectra.

The optical rotation was measured using a Perkin Elmer 1541 polarimeter having a cell depth of 10 cm. The FAB-MS spectra (direct inlet, positive ions) were recorded using a Jeol JMS-SX-102 spectrometer. $^1$H-NMR (500 MHz) and $^{13}$C-NMR (125 MHz) spectra were recorded at room temperature using a Bruker ARX 500 spectrometer with an inverted 5 mm sample head fitted with a shielded gradient coil. The gradient COSY, HMQC and HMBC experiments were carried out using sinoidal gradient pulses; in the case of the heteronuclear 2D correlations spectroscopy, the development times were optimized for $^1J_{CH}$=145 Hz and $^2J_{CH}$=10 Hz. The crude data were transformed, and the spectra were evaluated using the standard Bruker UXNMR software (rev. 941 001).

With the aid of the COSY spectrum, the proton signals of the individual amino acids can be assigned based on the H—H couplings, starting with the NH or the α proton. By using the HMQC spectrum, it is then possible to assign the carbon signals in a corresponding manner. The sequence of the amino acids was assigned with the aid of the HMBC spectrum. In the HMBC spectrum, the α protons of two amino acids which are linked to each other are correlated to the same carbonyl carbon. The α protons thus show two correlation peaks to carbonyl carbons: one peak by two-bond coupling to the carbonyl carbon of its own amino acid and one peak by three-bond coupling to the carbonyl carbon of the N-linked amino acid.

The following structures were determined:

Omphalotin B:

Omphalotin C:

Omphalotin D:

The $^1$H and $^{13}$C signals were assigned as shown in the two tables below:

TABLE 1

$^1$H (500 MHz) NMR data (δ; multiplicity; J) for omphalotin B, C and D in CD$_3$OD, with the solvent signal (3.31 ppm) as reference. The coupling constant J is given in Hz.

| H | Omphalotin B | Omphalotin C | Omphalotin D |
|---|---|---|---|
| 1 | 6.95; d; 7.8 | 6.72/6.93; d; 7.9 | 6.72/6.93; d; 7.9 |
| 2 | 7.22; dd; 7.8, 8 | 7.22/7.17; dd; 8.8 | 7.22/7.17; dd; 8.8 |
| 3 | 6.87; dd; 7.5, 8 | 6.82/6.87; dd; 8.8 | 6.82/6.87; dd; 8.8 |
| 4 | 7.28; d; 7.5 | 7.26/7.28; d; 7.5 | 7.26/7.28; d; 7.5 |
| 7 | 5.53; s | 5.56/5.65; s | 5.56/5.65; s |
| 9a | 2.67; m | 2.66/2.48; m | 2.65/2.48; m |
| 9b | 2.52; m | 2.53/2.33; m | 2.52/2.32; m |
| 10 | 4.39; dd; 7.4, 8.6 | 4.42/5.15; m | 4.41/5.16; m |
| 12 | 2.70; s | 2.70/2.78; s | 2.70/2.78; s |
| 13 | 3.83; d; 10.8 | 4.41/3.89; d; 10.8 | 4.42/3.88; d; 10.8 |
| 14 | 2.30; m | 2.33/2.30; m | 2.32/2.29; m |
| 15 | 0.78; m | 0.77/0.82; m | 0.78/0.82; m |
| 16 | 0.78; m | 0.89/0.78; m | 0.89/0.78; m |
| 18 | 4.67; dd; 8.10 | 4.67/4.77; m | 4.68/4.78; m |
| 19 | 1.99; m | 1.99/2.07; m | 1.99/2.06; m |
| 20 | 0.84; m | 0.89/0.89; m | 0.87/0.90; m |
| 21a | 1.49; m | 1.47/1.46; m | 1.46/1.46; m |
| 21b | 1.35; m | 1.23/1.36; m | 1.22/1.37; m |
| 22 | 0.87; m | 0.88/0.87; m | 0.87/0.85; m |
| 24 | 3.17; s | 3.15/3.09; s | 3.15/3.09; s |
| 25 | 5.32; d; 10.8 | 5.29/5.23; d; 10.8 | 5.29/5.23; d; 10.8 |
| 26 | 2.27; m | 2.28/2.33; m | 2.29/2.33; m |
| 27 | 0.70; d; 6.8 | 0.68/0.73; d; 6.8 | 0.68/0.73; d; 6.8 |
| 28 | 0.89; m | 0.90/0.85; m | 0.93/0.85; m |
| 30 | 2.94; s | 2.91/2.94; s | 2.91/2.94; s |
| 31 | 5.30; d; 10.8 | 5.29/5.10; d; 10.8 | 5.28/5.08; d; 10.8 |
| 32 | 2.23; m | 2.25/2.31; m | 2.24/2.31; m |
| 33 | 0.74; m | 0.78/0.75; m | 0.77/0.75; m |
| 34 | 0.88; m | 0.90/0.93; m | 0.90/0.93; m |
| 36 | 3.12; s | 3.02/3.12; s. | 3.02/3.12; s |
| 37a | 4.87; d; 16.5 | 4.90/4.84; d; 17 | 4.88/4.83; d; 17 |
| 37b | 3.68; d; 16.5 | 3.68/3.67; d; 17 | 3.67/3.65; d; 17 |
| 39 | 3.17; s | 3.17/3.16; s | 3.15/3.14; s |

TABLE 1-continued

¹H (500 MHz) NMR data (δ; multiplicity; J) for omphalotin B, C and D in CD₃OD, with the solvent signal (3.31 ppm) as reference. The coupling constant J is given in Hz.

| H | Omphalotin B | Omphalotin C | Omphalotin D |
|---|---|---|---|
| 40 | 5.11; s | 5.13/5.15; s | 5.12/5.13; s |
| 42 | 1.01; s | 1.02/1.21; s | 1.02/1.20; s |
| 43 | 1.20; s | 1.08/1.25; s | 1.08/1.25; s |
| 45 | 2.78; s | 2.83/2.76; s | 2.82/2.76; s |
| 46 | 5.20; d; 11 | 5.53/5.20; d; 10.9 | 5.55/5.22; d; 10.9 |
| 47 | 2.24; m | 2.25/2.28; m | 2.24/2.27; m |
| 48 | 1.10; d; 6.5 | 1.00/1.07; m | 0.99/1.05; m |
| 49 | 4.73; m | 4.68/4.69; m | 4.62/4.65; m |
| 50 | 1.30; d; 6.5 | 1.31/1.29; m | 1.30/1.28; m |
| 52 | 2.67; s | 2.70/3.06; s | 2.70/3.06; s |
| 53 | 6.36; s | 7.01/7.23; s | 7.02/7.24; s |
| 55 | 4.79; m | 4.81/4.55; d; 7.8 | 4.81/4.55; d; 7.8 |
| 56 | 1.91; m | 2.00/2.08; m | 2.00/2.08; m |
| 57 | 0.74; m | 0.76/1.01; m | 0.76/1.01; m |
| 58 | 0.29; d; 6.5 | 0.32/0.96; d; 6.5 | 0.32/0.97; d; 6.5 |
| 60 | 3.10; s | 3.06/3.18; s | 3.06/3.18; s |
| 61 | 5.18; d; 11 | 5.43/5.16; d; 10.8 | 5.42/5.15; d; 10.8 |
| 62 | 2.18; m | 2.16/2.18; m | 2.16/2.18; m |
| 63 | 0.86; m | 0.85/1.02; m | 0.85/1.02; m |
| 64a | 1.28; m | 1.25/1.07; m | 1.24/1.07; m |
| 64b | 1.28; m | 1.25/1.35; m | 1.24/1.35; m |
| 65 | 0.95; m | 0.86/0.83; m | 0.86/0.83; m |
| 67 | 2.83; s | 2.83/3.38; s | 2.82/3.38; s |
| 68a | 5.15; d; 17.3 | 5.05/5.14; d; 17 | 5.04/5.14; d; 17 |
| 68b | 4.25; d; 17.3 | 3.77/4.26; d; 17 | 3.77/4.25; d; 17 |
| 71 | 2.52; m | 2.52/2.52; m | 2.04/2.02; m |
| 73 | 1.32; s | 1.32/1.33; s | — |
| 74 | 1.32; s | 1.32/133; s | — |
| 76 | — | 2.17/2.27; s | 2.17/2.27; s |
| 17-NH | 8.17; d; 7.9 | 8.40; d; 9.0/8.18; d; 7.9 | 8.40; d; 9.0/8.18; d; 7.8 |

TABLE 2

¹³C (125 MHz) NMR data (δ; multipticity) for omphalotin B, C and D in CD₃OD, with the solvent signal (49.15 ppm) as reference.

| C | Omphalotin B | Omphalotin C | Omphalotin D |
|---|---|---|---|
| 1 | 113.4; d | 112.2/113.2; d | 112.2/113.2; d |
| 2 | 131.4; d | 131.2/131.4; d | 131.2/131.4; d |
| 3 | 121.2; d | 120.8/121.2; d | 120.8/121.2; d |
| 4 | 124.3; d | 124.0/124.3; d | 124.0/124.3; d |
| 5 | 131.5; s | 131.5/131.8; s | 131.5/131.8; s |
| 6 | 150.9; s | 150.0/150.8; s | 150.0/150.8; s |
| 7 | 83.3; d | 83.6/86.6; d | 83.6/86.6; d |
| 8 | 88.8; s | 88.9/90.2; s | 88.9/90.2; s |
| 9 | 41.6; t | 41.9/43.2; t | 41.9/43.2; t |
| 10 | 57.7; d | 57.9/58.3; d | 57.9/58.4; d |
| 11 | 174.7; s | 175.0/176.2; s | 175.0/176.2; s |
| 12 | 30.2; q | 30.2a/30.3; q | 30.3ᵈ/30.4; q |
| 13 | 67.9; d | 67.8/67.9; d | 67.9/67.9; d |
| 14 | 27.2; d | 27.2/27.4; d | 27.2/27.4; d |
| 15 | 19.8; q | 18.1/19.4; q | 18.1/19.4; q |
| 16 | 20.6; q | 20.1/20.5; q | 20.1/20.5; q |
| 17 | 169.8; s | 169.9/170.1; s | 169.9/170.1; s |
| 18 | 54.3; d | 54.4/54.6; d | 54.4/54.6; d |
| 19 | 35.9; d | 36.0/37.2; d | 36.0/37.2; d |
| 20 | 15.3; q | 15.7/16.3; q | 15.3/15.8; q |
| 21 | 26.4; t | 26.1/26.2; t | 26.1/26.2; t |
| 22 | 9.6; q | 9.8/11.4; q | 9.8/11.4; q |
| 23 | 174.7; s | 174.3/174.6; s | 174.3/174.6; s |
| 24 | 31.1; q | 30.9/31.1; q | 30.9/31.1; q |
| 25 | 59.6; q | 59.8/60.0; q | 59.8/60.0; q |
| 26 | 28.7; d | 28.4/28.6; d | 28.4/28.6; d |
| 27 | 9.1; q | 18.3/18.9; q | 18.3/18.9; q |
| 28 | 20.1; q | 19.8/20.3; q | 20.2/20.6; q |
| 29 | 172.4; s | 171.3/172.2; s | 171.3/172.2; s |
| 30 | 31.2; q | 31.0/31.3; q | 31.0/31.3; q |
| 31 | 58.8; d | 58.6/60.2; d | 58.8/60.2; d |
| 32 | 27.6; d | 27.6/27.8; d | 27.6/27.8; d |
| 33 | 18.3; q | 18.1/18.6; q | 18.1/18.6; q |
| 34 | 19.8; q | 19.8/20.7; q | 19.8/20.7; q |
| 35 | 172.8; s | 171.4/172.6; s | 171.4/172.6; s |
| 36 | 38.4; q | 37.6/38.3; q | 37.6/38.3; q |
| 37 | 51.3; t | 51.2/51.6; t | 51.2/51.6; t |
| 38 | 169.9; s | 170.0/170.4 | 170.0/170.4 |
| 39 | 33.2; q | 33.2/33.4; q | 33.3/33.4; q |
| 40 | 60.4; d | 59.3/60.3; d | 59.2/60.4; d |
| 41 | 75.5; s | 75.4/75.5; s | 75.3/75.5; s |
| 42 | 26.2; q | 26.1126.2; q | 26.1/26.2; q |
| 43 | 29.2; q | 29.3/29.4; q | 29.3/29.4; q |
| 44 | 172.8; s | 172.9/173.2; s | 172.9/173.2; s |
| 45 | 31.7; q | 30.9ᵇ/31.3; q | 30.9ᵉ/31.3; q |
| 46 | 59.4; q | 55.6/58.8; q | 55.6/58.8; q |
| 47 | 37.6; d | 37.9/38.3; d | 37.6/37.9; d |
| 48 | 11.2; q | 10.4/11.2; q | 10.4/11.1; q |
| 49 | 70.4; d | 70.3/70.3; d | 70.4/70.4; d |
| 50 | 18.2; q | 17.9/18.2; q | 17.9/18.1; q |
| 51 | 170.8; s | 170.4/171.0; s | 170.6/171.1; s |
| 52 | 28.2; q | 29.4ᵃ/31.0ᶜ; q | 29.4ᵈ/31.0ᶠ; q |
| 53 | 77.0; d | 76.8/77.0; d | 76.9/77.0; d |
| 54 | 169.3; q | 166.6/167.4; s | 166.5/167.4; s |
| 55 | 56.1; d | 56.5/56.8; d | 56.5/56.7; d |
| 56 | 31.2; d | 30.9/31.9; d | 30.9/31.9; d |
| 57 | 18.7; q | 18.1/18.6; q | 18.1/18.6; q |
| 58 | 18.9; q | 19.1/19.7; q | 9.1/19.7; q |
| 59 | 174.6; s | 174.2/174.2; s | 174.1/174.2; s |
| 60 | 31.6; q | 31.4ᶜ/31.5; q | 31.4ᶠ/31.5; q |
| 61 | 59.0; d | 56.7/58.8; d | 56.8/59.2; d |
| 62 | 35.4; d | 34.4/35.1; d | 34.4/34.5; d |
| 63 | 16.4; q | 16.4/17.2; q | 16.4/17.2; q |
| 64 | 24.7; t | 25.8/25.8; t | 25.4/25.8; t |
| 65 | 11.4; q | 10.6/11.3; q | 10.6/11.3; q |
| 66 | 171.9; s | 171.9/173.2; s | 171.9/173.2; s |
| 67 | 35.1; q | 35.0ᵇ/38.9; q | 35.1ᵉ/38.9; q |
| 68 | 53.2; t | 51.7/53.2; t | 51.7/53.2; t |
| 69 | 170.2; s | 170.2/170.9; s | 170.2/170.9; s |
| 70 | 172.9; s | 172.6/173.2; s | 172.7/172.9; s |
| 71 | 49.1; t | 49.0/49.0; t | 21.5/21.6; q |
| 72 | 70.4; s | 70.3/70.4; s | — |
| 73 | 29.5; q | 29.6/29.6; q | — |
| 74 | 29.6; q | 29.6/29.6; q | — |
| 75 | — | 170.3/170.6; s | 70.3/70.6; s |
| 76 | — | 20.4/20.6; q | 20.5/20.7; q |

ᵃ, ᵇ, ᶜ, ᵈ, ᵉ, ᶠ exchangeable

The structures of the novel compounds according to the invention were determined by extensive analytical, in particular spectroscopic, studies. However, since errors in the interpretation of the analytical data of substances of complex structure cannot always be totally excluded, the omphalotins are additionally described by some characteristic physico-chemical data and spectra:

TABLE 3

| | Omphalotin B | Omphalotin C | Omphalotin D |
|---|---|---|---|
| Appearance | white crystals | white crystals | white crystals |
| Melting point | 180–183° C. | 173–178° C. | 165–170° C. |
| Empirical formula | $C_{74}H_{123}O_{18}N_{13}$ | $C_{76}H_{125}O_{19}N_{13}$ | $C_{73}H_{119}O_{18}N_{13}$ |
| Molecular weight | 1483 | 525 | 1467 |
| Optical rotation $[\alpha]D_{22}$ (c2.0 in CH₃OH) | −246° | −242° | −254° |
| Spectra | see Tables 1 and 2 | | |

According to the invention, the novel omphalotins are produced by the fermentation of suitable strains of microorganisms from the class of the Basidiomycetes, in particular of the orders Omphalotus and Lampteromyces, preferably *Omphalotus olearius* and very particularly preferably of the *Omphalotus olearius* strains 83 039 (DSM 9737), 90 173 (DSM 9738), 91 050 (DSM 9739), 92 095 (DSM 9740), 93 162 (DSM 9741) or 90 170 (DSM 9742) or by mutants or variants thereof.

The fermentation process according to the invention is carried out in a customary manner. It can be carried out with the aid of solid, semi-solid or liquid culture media. Preference is given to using aqueous-liquid culture media.

The culture media are inoculated by customary methods, for example using oblique tubes or flask cultures.

The cultivation is carried out under aerobic conditions and can be carried out according to customary methods, for example by using shaking cultures for example in shaking flasks, by using air-agitated cultures or submersion cultures. Preference is given to carrying out the cultivation using the aerobic submersion process in aerated fermenters, for example in customary submersion fermentation tanks. The cultivation can be carried out continuously or batchwise. Preference is given to batchwise operation.

The cultivation can be carried out in all culture media which are known to be used for the cultivation of microorganisms of the class of the Basidiomycetes. The culture medium must contain one or more assimilable carbon sources and nitrogen sources and mineral salts, it being possible for these products to be present in the form of defined individual components, or else in the form of complex mixtures, as represented in particular by biological products of diverse origin. Suitable carbon sources are all customary carbon sources. Examples include carbohydrates, in particular polysaccharides, such as starch or dextrins, disaccharides, such as maltose or cane sugar, monosaccharides such as glucose or xylose, sugar alcohols such as mannitol or glycerol and naturally occurring mixtures such as malt extract, molasses or whey powder. Suitable nitrogen sources are all customary organic and inorganic nitrogen sources. Examples include proteins, protein hydrolysates, amino acids such as glutamic acid, glycine, aspartic acid, arginine, lysine, ornithine or serine, nucleoside bases such as cytosine or uracil and soya bean meal, cotton seed meal, lentil meal, pea meal, soluble and insoluble plant proteins, maize steep liquor, yeast extract, peptones and meat extract and also ammonium salts and nitrates, for example $NH_4Cl$, $(NH_4)_2SO_4$, $NaNO_3$ and $KNO_3$. The mineral salts which should be present in the culture medium generate, for example, the following ions:

$Mg^{++}$, $Na^+$, $K^+$, $Ca^{++}$, $NH_4^+$, $Cl^-$, $SO_4^{--}$, $PO_4^{--}$ and $NO_3^-$ and ions of the customary trace elements, such as Cu, Fe, Mn, Mo, Zn, Co, Ni. If the carbon or nitrogen sources or the water used do not contain enough of these salts or trace elements it is useful to supplement the culture medium appropriately. The composition of the culture media can vary within wide ranges. The kind and the composition of the culture media will generally depend on which components are in each case available at particularly low cost. In general, the culture solutions contain preferably about 0.5 to 8%, in particular 0.6 to 6%, of carbon sources, preferably about 0.5 to 4%, in particular 0.5 to 2%, of nitrogen sources and preferably about 0.001 to 0.5%, in particular 0.003 to 0.3%, of mineral salts.

When carrying out the process, it may be advantageous to use only relatively low concentrations of the soluble culture solution components at the beginning of the cultivation, and to feed these components in the form of sterile, relatively concentrated solution a fraction at a time to the culture broth by relatively frequent addition over the first 3 days of cultivation.

The pH of the growing cultures should preferably be maintained at between about 5 and about 10, in particular between 3.0 and 8.0. An unacceptably large decrease in pH into the acid range can be avoided by addition of an organic or inorganic base, preferably $CaCO_3$. As is customary in fermentation technology, it is also possible to carry out an automatic pH regulation where sterile organic or inorganic acid, for example $H_2SO_4$, or sterile liquor, for example NaOH, is injected into the culture broth at intervals.

It is useful to make sure that the microorganisms are in sufficient contact with oxygen and the nutrients. This can be ensured by customary methods such as shaking and stirring.

The cultivation temperature may be between about 15 and about 40° C., preferably between 20 and 35° C., particularly preferably, the temperature is between about 22 and 30° C. The duration of the cultivation can vary within wide limits, depending, for example, on the composition of the culture medium and the cultivation temperature. The particular optimum conditions can easily be determined by any person skilled in the art of microbiology.

It has been found that the amount of the compounds according to the invention which becomes enriched in the cultivation broth generally reaches its maximum after about 1 to 10, preferably about 4 to 7, days after the beginning of the cultivation. The desired end products of fermentation can be determined with the aid of thin-layer-chromatographical studies, with the aid of HPLC and UV absorption spectra or by the nematicidal or insecticidal activity.

As in all microbiological processes, extraneous infections of the culture media should be avoided. For this purpose, the usual precautions are taken, such as sterilization of the culture media, of the culture vessels and of the air required for aeration. For the sterilization of the equipment, it is for example possible to use both steam and dry sterilization, the temperatures preferably being at 100 to 140° C., in particular at 120 to 130° C.

If foam is formed in undesirable quantities during the cultivation, the customary chemical defoamers, for example liquid fats and oils, oil-water emulsions, paraffins, higher alcohols, such as octadecanol, silicone oils, polyoxyethylene or polyoxypropylene compounds (for example in amounts of up to about 1%) may be added. Foam may also be reduced or eliminated with the aid of the customary mechanical devices (which use, for example, centrifugal forces).

The compounds according to the invention can be isolated by customary physico-chemical methods from the culture medium and from the biomass. The isolation may be carried out for example by the customary extraction processes, precipitation processes and/or chromatographic processes. The fine purification of the particular isolated substance may also be carried out with the aid of the abovementioned methods. However, in many cases a fine purification is not necessary, since minor impurities which may be present do not adversely affect the activity of the compounds.

When carrying out the abovementioned isolation and purification methods, the customary physico-chemical methods, for example measuring of a characteristic band in the spectrum or of the $R_f$ values, determination of the nematicidal and insecticidal activity, etc., may be employed to find the fractions in which the compounds according to the invention are present in the highest concentration or purity. These methods can also be employed to find suitable microorganisms by routine processes.

The isolation and purification of the compounds according to the invention, for example in the case where a liquid aqueous culture medium is used, can be carried out as follows:

After it is enriched in the supernatant of the culture, culture filtrate and mycelium are separated by customary methods (for example centrifugation).

The compounds according to the invention can be isolated, and, if appropriate, purified, from the culture filtrate, preferably from the biomass, with the aid of customary extraction processes, precipitation processes and/or chromatographic processes. Chromatography can be carried out in the form of column chromatography.

Suitable for use as adsorbents are the customary inorganic or organic adsorbents, such as, for example, alumina, silica gel, magnesium silicate, activated charcoal, cellulose, cellulose derivatives, synthetic resins such as polyamides, for example acetylated polyamide, dextran gels or modified dextran gels. Suitable for use as eluents are all the different solvents or solvent mixtures in which the compounds according to the invention is soluble. Preference is given to using water, ammonia solution, chloroform and methanol or mixtures thereof (for example mixtures of chloroform, methanol and aqueous $NH_3$ or methanol and water).

For the isolation of the compounds according to the invention, preference is given to using chromatographic processes, for example non-specific adsorption on sorbents such as silica gel, ion-exchange chromatography or gel-diffusion chromatography. These are methods which are known from the purification of water-soluble charged natural compounds.

Furthermore, the method of vacuum-liquid chromatography on diols may also be employed advantageously. In this case, hexane/ethyl acetate is suitably used as solvent mixture.

The compounds according to the invention can be obtained from their solutions by customary methods, for example by the evaporation of the solvent, freeze-drying, etc.

In a preferred embodiment of the invention, the biomass (the mycelium) is obtained by centrifugation of the fermentation material (culture broth and mycelium) which is obtained during the aerobic cultivation of the strains at about 27° C.

The novel substances are preferably obtained by extraction of the biomass.

The crude product is taken up in water and, after insoluble components have been separated off, purified further by customary chromatographic processes. Preference is given to a purification of the active fractions by chromatography (for example Sephadex LH 20). The novel substances are finally prepared in pure form by chromatographic methods, preferably by silica-gel chromatography and preparative HPLC.

The compound according to the invention is suitable for controlling animal pests, in particular insects, arachnids and nematodes, encountered in agriculture, in forests, in the protection of stored products and of materials, and in the hygiene sector. They can preferably be used as crop protection agents. They are active against normally sensitive and resistant species and against all or some stages of development. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis, Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp., Linognathus spp.

From the order of the Mallophaga, for example, Trichodectes spp., Damalinea spp.

From the order of the Thysanoptera, for example, *Hercinothrips femoralis, Thrips tabaci.*

From the order of the Heteroptera, for example, Eurygaster spp., *Dysdercus intermedius, Piesma quadrata, Cimex lectularius, Rhodnius prolixus,* Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica.*

From the order of the Hymenoptera, for example, Diprion spp., Hoplocampa spp., Lasius spp., *Monomorium pharaonis,* Vespa spp.

From the order of the Diptera, for example, Aedes spp., Anopheles spp., Culex spp., *Drosophila melanogaster,*

Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderna spp., Tabanus spp., Tannia spp., *Bibio hortulanus, Oscinella frit*, Phorbia spp., *Pegomyia hyoscyami, Ceratitis capitata, Dacus oleae, Tipula paludosa.*

From the order of the Siphonaptera, for example, *Xenopsylla cheopis*, Ceratophyllus spp.

From the order of the Arachnida, for example, *Scorpio maurus, Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp.

The phytoparasitic nematodes include, for example, Pratylenchus spp., *Radopholus similis, Ditylenchus dipsaci, Tylencliulus semipenetrans*, Heterodera spp., Globodera spp., Meloidogyne spp., Aphelenchoides spp., Longidorus spp., Xiphinema spp., Trichodorus spp.

The compounds of the formula (I) according to the invention in particular have outstanding nematicidal activity, for example against *Meloidogyne incognita*, and activity against animal-pathogenic helminths.

In ranges of up to about 50 to 100 µg/ml, the compounds according to the invention do not have any cytotoxic, haemolytic and, in the case of plants, no germination-inhibiting or growth-inhibiting activity.

They have systemic action and can also be applied via the leaves.

The active compounds can be converted to the customary formulations, such as solutions, emulsions, wettable powders, suspensions, powders, dusting agents, pastes, soluble powders, granules, suspo-emulsion concentrates, natural and synthetic materials impregnated with active compound and very fine capsules in polymeric substances.

These formulations are produced in a known manner, for example by mixing the active compound with extenders, that is liquid solvents and/or solid carriers, if appropriate with the use of surfactants, that is emulsifiers and/or dispersants and/or foam-formers.

If the extender used is water, it is also possible to use for example organic solvents as auxiliary solvents. Suitable liquid solvents are essentially: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, for example mineral oil fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide and water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol, polyvinyl acetate, and natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide, Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas, substances produced by microorganisms, inter alia.

Examples of particularly advantageous mixing components are the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloroN-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cypro-conazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, toiclophos-methyl, tolylfluanid, triadimefon, triadimenol, triazoxide, trichiamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides/Anthelmintics:

abamectin, AC 303 630, acephate, acrinathrin, alanycarb, albendazole, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, bithionol, BPMC, brofenprox, bromophos A, bufencarb, buprofezin, butocarboxin, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, chlorsulon, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, doramectin, edifenphos, emamectin, eprinomectin, epsiprantel, esfenvalerate, ethiofencarb, ethion, ethofenprox, ethoprophos, etrimfos, febantel, fenamiphos, fenazaquin, fenbendazole, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, levamisol, lufenuron, malathion, mebendazole, mecarbam, mervinphos, mesulfenphos, metaldehyde, methacrifos, methamidophos, methidathion, methiocarb, methomyl, metolcarb, metrifonat, milbemectin, milbemycin, monocrotophos, morantel, moxidectin, naled, NC 184, NI 25, naphthalofos, niclofolan, niclosamide, nitenpyram, omethoate, oxamyl, oxantel, oxydemeton M, oxydeprofos, parathion A, parathion M, permethrin, PF 1022, PF 1022-221, phenthoate, phorate, phosalone, phosmet, phosphamidon, phoxim, pirimicarb, pirimiphos M, pirimiphos A, peraziquantel, profenofos, promecarb, propaphos, propoxur, prothiofos, prothoate, pymetrozine, pyrachlophos, pyradaphenthion, pyrantel, pyresmethrin, pyrethrum, pyridaben, pyrimidifen, pyriproxifen, pyrvinium, quinalphos,

RH 5992, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiabendazole, thiafenox, thiodicarb, thiofanox, thiomethon, thionazin, thuringiensin, tralomethrin, triarathene, triazophos, triazuron, trichlorfon, triclabendazole, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compounds according to the invention can furthermore be present in its commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms. The active compounds can be applied to above-ground parts of plants, or via the soil. Treatment of seed is also possible.

When used against hygiene and stored-product pests, the active compounds have an excellent residual action on wood and clay and a good stability to alkali on limed substrates.

Having favourable toxicity to warm-blooded species, the active compounds are suitable for controlling pathogenic endoparasites which occur in humans and in particular in animal keeping and animal breeding, in productive animals, breeding animals, zoo animals, laboratory animals, animals for experimentation and pets. They are active against all or individual stages of development of the pests and against resistant and normally sensitive species. By controlling the pathogenic endoparasites the intention is to reduce disease, mortality and reductions in yield (for example in the production of meat, milk, wool, hides, eggs, honey, etc.), so that the use of the active compounds enables more economical and simpler animal keeping. The pathogenic endoparasites include cestodes, trematodes, nematodes and acantocephalans, in particular:

From the order of the Pseudophyllidea, e.g.: Diphyllobothrium spp., Spirometra spp., Schistocephalus spp., Ligula spp., Bothridium spp., Diphlogonoporus spp.

From the order of the Cyclophyllidea, e.g.: Mesocestoides spp., Apoplocephala spp., Paranoplocephala spp., Moniezia spp., Thysanosomasa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, e.g.: Gyrodactylus spp., Dactylogyrus spp., Polystoma spp.

From the subclass of the Digenea, e.g.: Diplostomum spp., Posthodiplostomum spp., Schistomsoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiochis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonismus spp.

From the order of the Enoplida e.g.: Trichuris spp., Capillaria spp., Trichomosoides spp., Trichinella spp.

From the order of the Rhabditia e.g.: Micronema spp., Strongyloides spp.

From the order of the Strongylida e.g.: Strongylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida e.g.: Oxyuris spp., Enterobius spp., Passalurus spp., Syphacia spp., Aspiculuris spp., Heterakis spp.

From the order of the Ascaridia e.g.: Ascaris spp., Toxascaris spp., Toxocara spp., Parascaris spp., Anisakis spp., Ascaridia spp.

From the order of the Spirurida e.g.: Gnathostoma spp., Physaloptera spp., Thelazia spp., Gongylonema spp., Habronema spp., Parabronema spp., Draschia spp., Dracunculus spp.

From the order of the Filariida e.g.: Stephanofilaria spp., Parafilaria spp., Setaria spp., Loa spp., Dirofilaria spp., Litomosoides spp., Brugia spp., Wuchereria spp., Onchocerca spp.

From the order of Gigantorhynchida e.g.: Filicollis spp., Moniliformis spp., Macracanthorhynchus spp., Prosthenorchis spp.

The productive and breeding animals include mammals such as cattle, horses, sheep, pigs, goats, camels, water buffalo, donkeys, rabbits, fallow deer, reindeer, fur-bearing animals such as mink, chinchilla, raccoon, birds such as chicken, geese, turkeys, ducks, fresh- and salt-water fish such as trout, carp, eels, reptiles, insects such as honey-bee and silkworm.

Laboratory and experimental animals include mice, rats, guinea-pigs, golden hamsters, dogs and cats.

The pets include dogs and cats.

Administration can be carried out both prophylactically and therapeutically.

Administration of the active compounds is carried out directly or in the form of suitable preparations, enterally, parenterally, dermally, nasally, by treating the habitat or with the aid of active compound-containing shaped articles such as, for example, stripes, plates, bands, collars, ear-tags, straps for limbs, marking devices.

Enteral administration of the active compounds is carried out, for example, orally in the form of powders, tablets, capsules, pastes, drinks, granules, orally administrable solutions, suspensions and emulsions, boluses, medicated feed or drinking water. Dermal administration is carried out, for example, in the form of dipping, spraying or pouring-on and spotting-on. Parenteral administration is carried out, for example, in the form of injections (intramuscular, subcutaneous, intravenous, intraperitoneal), or by implants.

Suitable preparations are:

solutions such as solutions for injection, oral solutions, concentrates for oral administration after dilution, solutions for use on the skin or in body cavities, pouring-on formulations, gels;

emulsions and suspensions for oral or dermal administration and for injection; semi-solid preparations;

formulations in which the active compound is processed in an ointment base or in an oil-in-water or water-in-oil emulsion base;

solid preparations such as powders, premixes or concentrates, granules, pellets, tablets, boluses, capsules; aerosols and inhalants, active compound-containing shaped articles.

Solutions for injection are administered intravenously, intramuscularly and subcutaneously.

Solutions for injection are prepared by dissolving the active compound in a suitable solvent and adding, if appropriate, additives such as solubilizers, acids, bases, buffer salts, antioxidants, preservatives. The solutions are filtered and filled under sterile conditions.

Solvents which may be mentioned are: physiologically tolerable solvents such as water, alcohols such as ethanol, butanol, benzyl alcohol, glycerol, propylene glycol, polyethylene glycols, N-methyl-pyrrolidone, and mixtures thereof.

The active compounds can optionally also be dissolved in physiologically tolerable vegetable or synthetic oils which are suitable for injection.

Solubilizers which may be mentioned are: solvents which promote the dissolution of the active compounds in the main solvent or prevent its precipitation. Examples are polyvinylpyrrolidone, polyethoxylated castor oil, polyethoxylated sorbitan ester.

Preservatives are: benzyl alcohol, trichlorobutanol, p-hydroxybenzoic acid esters, n-butanol.

Oral solutions are administered directly. Concentrates are administered orally after prior dilution to the use concentration. Oral solutions and concentrates are prepared as described above for the solutions for injection, sterile procedures not being necessary.

Solutions for use on the skin are trickled on, spread on, rubbed in, sprinkled on or sprayed on. These solutions are prepared as described above for the solutions for injection.

It may be advantageous to add thickeners during preparation. Thickeners are: inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the solutions for injections with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone, 2,2-dimethyl-4-oxy-methylene-1,3-dioxolane.

Colorants are all colorants permitted for use on animals and which can be dissolved or suspended.

Absorption-promoting substances are, for example, DMSO, spreading oils such as isopropyl myristate, dipropylene glycol pelargonate, silicone oils, fatty acid esters, triglycerides, fatty alcohols.

Antioxidants are sulfites or metabisulfites such as potassium metabisulfite, ascorbic acid, butylhydroxytoluene, butylhydroxyanisole, tocopherol.

Light stabilizers are, for example, novantisolic acid.

Adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the particular active compound either in the hydrophobic or in the hydrophilic phase and homogenizing this with the solvent of the other phase with the aid of suitable emulsifiers and, if appropriate, other auxiliaries such as colorants, bioabsorption-promoting substances, preservatives, antioxidants, light stabilizers, viscosity-enhancing substances.

Hydrophobic phases (oils) which may be mentioned are: paraffin oils, silicone oils, natural vegetable oils such as sesame oil, almond oil, castor oil, synthetic triglycerides such as caprylic/capric biglyceride, triglyceride mixture with vegetable fatty acids of the chain length $C_{8-12}$ or other specially selected natural fatty acids, partial glyceride mixtures of saturated or unsaturated fatty acids possibly also containing hydroxyl groups, mono- and diglycerides of the $C_8/C_{10}$ fatty acids.

Fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, ester mixtures related to the latter, inter alia.

Fatty alcohols such as isotridecyl alcohol, 2-octyldodecanol, cetylstearyl alcohol, oleyl alcohol.

Fatty acids such as oleic acid and its mixtures.

Hydrophilic phases which may be mentioned are:
water, alcohols such as propylene glycol, glycerol, sorbitol and its mixtures.

Emulsifiers which may be mentioned are: non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-Na N-lauryl-β-iminodipropionate or lecithin;
anionic surfactants, such as Na lauryl sulphate, fatty alcohol ether sulphates, mono/dialkyl polyglycol ether orthophosphoric acid ester monoethynolamine salt.

Further auxiliaries which may be mentioned are: viscosity-enhancing substances which stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally, dermally or as injection. They are prepared by suspending the particular active compound in a liquid excipient, if appropriate with addition of other auxiliaries such as wetting agents, colorants, resorption-promoting substances, preservatives, antioxidants light stabilizers.

Liquid excipients which may be mentioned are all homogeneous solvents and solvent mixtures.

Wetting agents (dispersants) which may be mentioned are the surfactants given above.

Other auxiliaries which may be mentioned are those given above.

Semi-solid preparations can be administered orally or dermally. They differ from the suspensions and emulsions described above only by their higher viscosity.

For the production of solid preparations, the particular active compound is mixed with suitable excipients, if appropriate with addition of auxiliaries, and brought into the desired form.

Excipients which may be mentioned are all physiologically tolerable solid inert substances. Those used are inorganic and organic substances. Inorganic substances are, for example, sodium chloride, carbonates such as calcium carbonate, hydrogencarbonates, aluminium oxides, silicic acids, argillaceous earths, precipitated or colloidal silica, phosphates.

Organic substances are, for example, sugar, cellulose, foodstuffs and feeds such as milk powder, animal meal, grain meals and shreds, starches.

Auxiliaries are preservatives, antioxidants, colorants which have already been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

The active compounds can also be present in the preparations as a mixture with synergists or with other active compounds which act against pathogenic endoparasites. Such active compounds are, for example, L-2,3,5,6-tetrahydro-6-phenylimidazothiazole, benzimidazole carbamates, praziquantel, pyrantel, febantel.

Ready-to-use preparations contain the particular active compound in concentrations of 10 ppm–20 percent by weight, preferably of 0.1–10 percent by weight.

Preparations which are diluted before use contain the active compound in concentrations of 0.5–90% by weight, preferably of 5–50% by weight.

In general, it has proven to be advantageous to administer amounts of about 1 to about 100 mg of active compound per kg of body weight per day to obtain effective results.

The preparation of the novel omphalotins and their biological properties are illustrated by the following examples.

In the examples (as in the rest of the description) percentages refer to percentages by weight and specifications of solvent mixtures refer to parts by volume, unless stated otherwise.

The test methods given in the examples are also particularly suitable to determine the fractions which contain the particular omphalotin in the production of omphalotins. They can also be employed to estimate the particular omphalotin content.

EXAMPLE 1

Preparation of the Omphalotins by Fermentation of *Omphalotus learius* No. 90 170=DSM 9742

1.1 Preparation of solid media agar plates for the cultivation of *Omphalotus olearius*
1.2 Cultivation of *Omphalotus olearius* on solid media agar plates
1.2 Preparation of the culture medium for the precultivation of *Omphalotus olearius*
1.4 Inoculation and cultivation of *Omphalotus olearius* in the preculture medium
1.5 Preparation of the culture medium for the fermentation of *Omphalotus olearius* in the main fermenter
1.6 Inoculation and cultivation of *Omphalotus olearius* in the main fermenter
1.7 Harvest of the biomass after the fermentation
1.1 Preparation of Solid Media Agar Plates for the Cultivation of *Omphalotus olearius*

For the preparation of solid media agar plates (M1 medium)
   4 g/l of glucose
   4 g/l of yeast extract (Merck No. 3753, 64271 Darmstadt, Germany)
   10 g/l of Löflund's barley malt extract (Dr. Fränkle & Max Eck, 70736 Fellbach, Germany)
   20 g/l of agar agar (Merck No. 1615, 64271 Darmstadt, Germany)
are weighed in, dissolved in demineralized water and adjusted to pH 5.5 by addition of acid (c(HCl)=2 mol/l). A 2 l Erlenmeyer flask is charged with 1 l of the abovementioned solution, sealed with a cottonwool plug and sterilized in an autoclave (MMM, type LSS 666-1) at a temperature of 121° C. for 20 minutes.

With continuous stirring, the solution is cooled to a temperature of about 50 to 60° C. 20 ml of the solution are transferred into 90 mm Petri dishes under sterile conditions. After the solution has cooled, the filled Petri dishes can be stored at room temperature for a maximum of 8 weeks prior to an inoculation.

1.2 Cultivation of *Omphalotus olearius* on Solid Media Agar Plates

The agar of a solid media agar plate which is densely colonized by *Omphalotus olearius* (in the present example No. 90 170) is divided under sterile conditions into pieces of a size of 1×1 cm with the aid of a scalpel. In each case one agar mycelium piece is transferred with a pair of tweezers onto a solid media agar plate as described under 1.1 (mycelium facing upwards) and incubated in an incubation cabinet (Heraeus, type BK 5060 E) at 27° C. in the dark for a maximum of 3 weeks. After 3 weeks have expired, the colonized plates can be used as inoculation plates for the fermentation, or they can be used once more for the inoculation of solid media agar plates.

1.3 Preparation of the Culture Medium for the Precultivation of *Omphalotus olearius*
   4 g/l of glucose
   4 g/l of yeast extract (Merck No. 3753, 64271 Darmstadt, Germany)
   10 g/l of Löflund's barley malt extract (Dr. Fränkle & Max Eck, 70736 Fellbach, Germany)
are weighed in, dissolved in demineralized water and adjusted to pH 5.5 by addition of acid (c(HCl)=2 mol/l). A 1 l Erlenmeyer flask is charged with 300 ml of the abovementioned solution, sealed with a cottonwool plug and autoclaved at 121° C. for 30 minutes. After cooling, the filled Erlenmeyer flasks are stored at room temperature for a maximum of 8 weeks prior to an inoculation.

1.4 Inoculation and Cultivation of *Omphalotus olearius* in the Preculture Medium In each case 300 ml of the culture medium described under 1.3 are inoculated with half of a densely populated 2- to 3-week-old solid media plate. To this end, 2- to 3-week-old solid media plates are divided under sterile conditions using a scalpel and transferred into a Waring mixer attachment (Waring Blender, type 32BL79) by means of a pair of tweezers. The solid media plates are mixed with 50 ml of sterile distilled water per solid media plate and homogenized for 30 seconds (15 seconds on low setting, 15 seconds on high setting). The total volume of the homogenized liquid is distributed evenly, using a 10 ml pipette (Becton Dickinson and Company, type Falcon), over the Erlenmeyer flask which had been prepared for inoculation. The incubation of the preculture flasks is carried out in the shaking cabinet (Braun Melsungen type BS 4) at a temperature of 27° C. and a shaking speed of 120 rpm for 5 to 6 days.

1.5 Preparation of the Culture Medium for the Fermentation of *Omphalotus olearius* in the Main Fermenter A 450 l fermenter (Braun Melsungen type Biostat 450 D) is filled with 320 l of demineralized water, and
   4 g/l of glucose
   4 g/l of Fermtech yeast extract (Merck No. 11926, 64271 Darmstadt, Germany)
   10 g/l of Löflund's barley malt extract (Dr. Fränkle & Max Eck, 70736 Fellbach, Germany)
   0.25 ml/l of A (Sigma-Aldrich Chemie GmbH, 89552 Steinheim)
are added, based on the operating volume of 350 l. After filling, the fermenter is closed and the content is sterilized at a temperature of 121° C. for 30 minutes. After cooling to an operating temperature of 27° C., an overpressure of 0.3 bar is applied and the aeration rate is set to 0.25 vvm. After the oxygen saturation has reached the maximum, the $pO_2$ meter is calibrated to an initial value of 99%. The pH of the medium is adjusted to 5.5 with the aid of acid (c(HCl)=2 mol/l).

1.6 Inoculation and Cultivation of Omphalotus olearius in the Main Fermenter

To this end, 151 l Erlenmeyer flasks each containing 300 ml of preculture are transferred under sterile conditions into a 5 l glass bottle (Schott) (the bottle is connected via a silicone tube with a tap set supplied by Braun Melsungen).

Using this tap set, the fermenter is, via a membrane in the lid, inoculated with the preculture in a sterile manner.

After the glucose concentration c(glucose) in the culture filtrate of the prefermenter (see 1.6) has dropped to $\leq 1$ g/l, the main fermenter is inoculated with the content of the prefermenter via sterile transfer tubing. The glucose concentration is determined using a Beckmann glucose analyser.

Fermentation conditions:

| | |
|---|---|
| Temperature | 27° C. |
| Stirring speed | 150 rpm |
| Aeration rate | 0.25 vvm |
| Pressure | 0.3 bar |
| pH | not controlled |
| Antifoam | as required |
| Incubation time | 6 to 7 days |

1.7 Harvest of the Biomass After the Fermentation

At a glucose concentration of c(glucose) $\leq 1$ g/l, the fermentation in the 450 l fermenter is terminated and the biomass is harvested. The content of the main fermenter is separated from the culture medium through gauze (Holthaus Medical, Verbandmull, Remscheid 11, Germany). The biomass filter off is washed repeatedly with demineralized water and subsequently centrifuged in a tumble drier (Miele, type MZ 5942, Germany) at 4000 rpm for 3 minutes. 3 to 6 kg of moist biomass are harvested. The Omphalotus olearius biomass obtained is frozen at a temperature of −34° C. and stored until further work-up.

The fermentation of the other Omphalotus strains can be carried out similarly to the example above.

EXAMPLE 2

Isolation and Purification of the Omphalotins B–D 2.1 Preparation of the Crude Extract of the Active Compounds from Omphalotus olearius and Enrichment of the Active Compounds by Extraction, Chromatography by the Principle of Gel Filtration and Vacuum-liquid Chromatography 100 l fermentation broth (see Example 1) give 480 g of lyophilized mycelia (freeze dryer Alpha I/20, Christ, Osterode). The mycelium is divided into 2 portions, and these are worked up separately.

240 g of lyophilized mycelia are comminuted in a mixer (Warring commercial blendor) and then extracted for 5 h with stirring, using 5 l of methanol. Using a Büchner funnel, the mycelium is separated from the solvent. Removal of the solvent by means of a rotary evaporator at 45° C. (Rotavapor R114, Büchi, Switzerland) gives 45 g of crude extract. This crude extract is dissolved in 250 ml of water and extracted four times with in each case 250 ml of ethyl acetate. The ethyl acetate phases are combined and the solvent is removed using a rotary evaporator at 45° C., giving 12 g of enriched crude product.

12 g of crude product are dissolved in 6 ml of methanol and chromatographed over a separation column (height: 77 cm, diameter: 2.5 cm) filled with Sephadex LH-20 (Pharmacia, Sweden), using dichloromethane/methanol (20:80) as mobile phase. The flow rate is adjusted so that 3 ml/min of eluate is obtained. The eluate is collected in 50 ml fractions. The fractions containing omphalotin are combined and evaporated using a rotary evaporator. This gives 1.2 g of enriched extract.

1.2 g of enriched extract are dissolved in 2 ml of cyclohexane and applied to a separating column (height: 8 cm, diameter: 2.5 cm). This is filled with modified silica gel (LiChroprep diol, particle size 25–40 μm, Merck, Darmstadt), which is equilibrated in cyclohexane. By applying a vacuum, the flow rate is adjusted to 4.4 ml/min. Elution is carried out using a stepwise gradient of 100% cyclohexane, 25%, 50%, 75% ethyl acetate in cyclohexane and 100% ethyl acetate, using 100 ml of solvent for each step. After evaporation of the solvent, 120 mg of product I (eluted with 75% of ethyl acetate and cyclohexane) and 80 mg of product II (eluted with 100% of ethyl acetate) are obtained.

2.4 Fine Separation by Preparative HPLC of the Enriched Active Compound Fractions Obtained from the Chromatographic Separations

| | |
|---|---|
| Apparatus: | Jasco PU-980 high-pressure pump fitted with LG-980-02 gradient mixer and multiwavelength detector MD-910 |
| Columns: | |
| Column 1: | Hibar RT LiChrospher RP 18 WP 300 ® (12 μm, 250 × 25 mm), Merck, Darmstadt, used with water/acetonitrile (isocratic) and a flow rate of 10 ml/min. |
| Column 2: | Hibar RT LiChrospher RP 18 ® (7 μm, 250 × 10 mm), Merck, Darmstadt, used with water/acetonitrile (isocratic) and a flow rate of 5 ml/min. |
| Detection = UV, λ = 210 nm | |

2.2.1 Fine Separation Product I

Product I (120 mg) is dissolved in 1 ml of methanol and filtered under sterile conditions (Chromofil® disposable filter type PES-45/15, pore diameter 0.45 μm, Macherey und Nagel, Düren) and chromatographed isocratically with water/acetonitrile (40:60) using column 1. Between the 20th and the 30th minute, 24 mg of a mixture of omphalotin D and C are eluted. This mixture is rechromatographed isocratically with water/acetonitrile (40:60) using column 2. This gives 10 mg each of partially purified omphalotin C (retention time: 9 minutes) and D (retention time: 11 minutes). These fractions are rechromatographed once more (column 2, isocratically with water/acetonitrile (45:55)). The pure active compound omphalotin C (7 mg) is obtained after 10 minutes, the pure active compound omphalotin D (7 mg) after 12 minutes.

Starting with 480 g of mycelia, 14 mg of omphalotin C and 14 mg of omphalotin D are obtained.

2.2.2 Fine Separation Product II:

Product II (80 mg) is dissolved in 1 ml of methanol and filtered under sterile conditions and chromatographed isocratically with water/acetonitrile (40:60) using column 1. Between the 14th and the 16th minute, omphalotin B is eluted. To increase the purity of the substance, it is rechromatographed isocratically with water/acetonitrile (40:60) over column 2. The pure active compound omphalotin B (11 mg) is obtained after 14 minutes.

Starting with 480 g of mycelia, 22 mg of omphalotin B are obtained.

2.3 Detection System for the Omphalotins B–D by Analytical High-pressure Liquid Chromatography (HPLC)

| Apparatus: | HP 1090, Series II, Hewlett-Packhard, Waldbronn, |
|---|---|
| Column: | LiChrospher 100 RP 18 endcapped (5 µm, 250–25 mm), Merck, Darmstadt |
| Solvent: | A: water, B: acetonitrile |
| Flow rate: | 1 ml/min |
| Column temperature: | 40° C. |
| Detection: | UV, λ = 210 nm |
| Amount injected: | 10 µl from 1 mg/ml of the sample material in methanol |
| Gradient: | |
| 0 min: | 0% B |
| 3 min: | 80% B |
| 13 min: | 80% B |
| 14 min: | 100% B |
| 19 min: | 100% B |
| 20 min: | 0% B |

The fractions to be analysed are concentrated using a rotary evaporator, taken up in acetonitrile and injected onto the column as a 0.1% solution.

The retention time for omphalotin B is 8.24 minutes, for omphalotin C it is 9.25 minutes and for omphalotin D 9.97 minutes.

Figure 1:
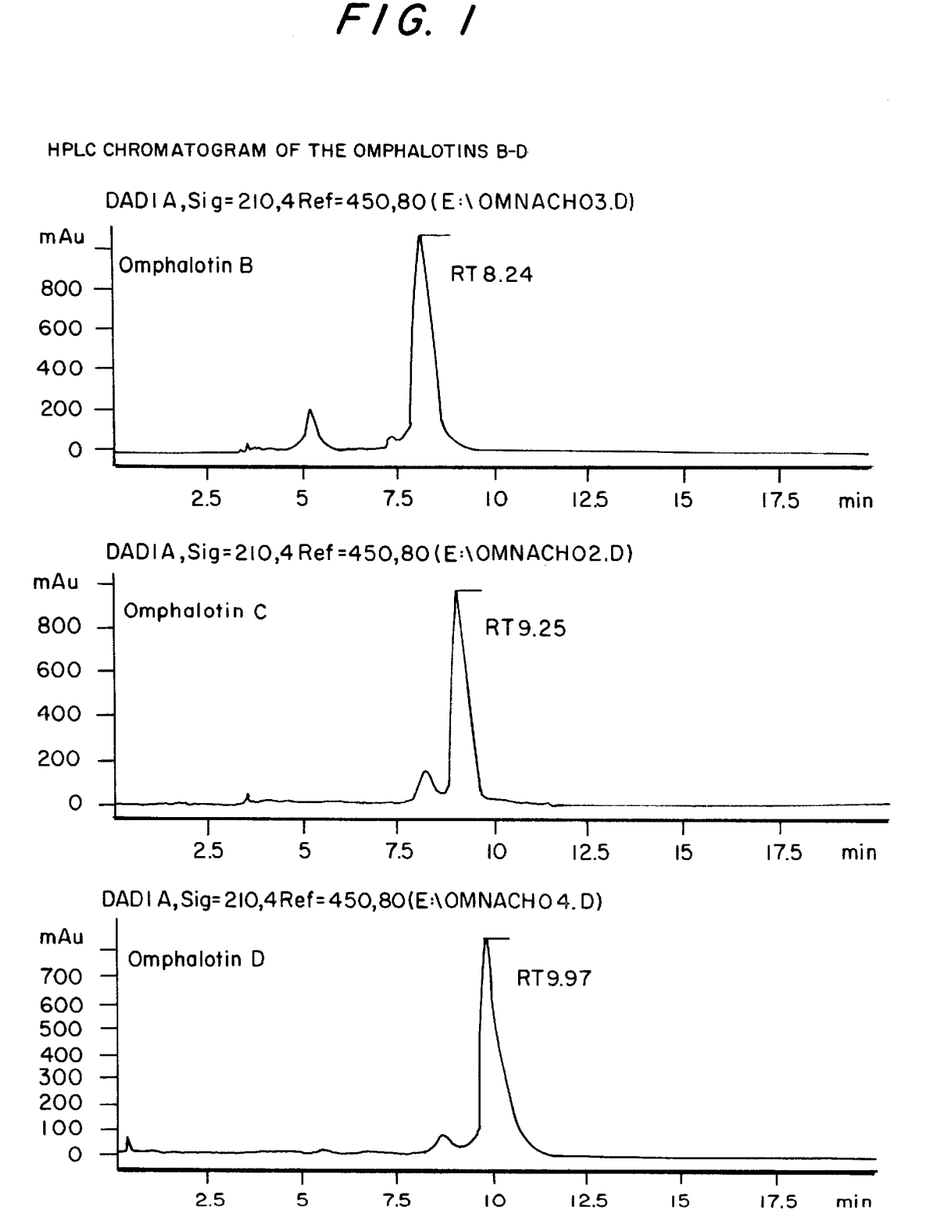
FIG. 1 represents the analytical high-pressure liquid chromatography (HPLC) profiles of omphalotins B–D obtained with a water:acetonitrile gradient system The retention time for omphalotin B is 8.24 minutes, for omphalotin C it is 9.25 minutes and for omphalotin D 9.97 minutes.

The chromatography profile of the analytical HPLC with the retention times is as shown in FIG. 1

Biological Characterization of the Omphalotins B–D

EXAMPLE A

Effect of the Substances Omphalotin B–D According to the Invention on Phytopathogenic Nematodes Test nematode: *Meloidogyne incognita*

Test method: The test substances are dissolved in methanol and pipetted into the wells of tissue culture plates (24-well tray). The solvent is evaporated, and 400 µl of nematode suspension are then added to each well of the tissue culture plate. The number of nematodes is 100 larvae of the second larval stage/400 µl . To promote the solubility of the samples in aqueous medium, the plate is shaken at 100 rpm for 15 minutes, and a first microscopic control is then carried out. After 16 hours, the percentage of dead larvae is determined and stated as $LD_{90}$ (lethal dose for 90% of the nematode population).

| Test substance | Nematicidal activity against *Meloidogyne incognita* [µg/ml] $LD_{90}$ |
|---|---|
| Omphalotin B | 2.5 |
| Omphalotin C | 1 |
| Omphalotin D | 4 |

EXAMPLE B

Effect of the Substance Omphalotin D According to the Invention on Insects

Test insect: *Plutella xylostella*

Test method: Using a cork borer, 2 discs having a diameter of 10 mm are punched out of savoy cabbage leaves and placed in a Petri dish (diameter 5.5 cm, Greiner). The test substance is pipetted onto the leaf discs and, after the solvent has evaporated, a filter disc (diameter 13 mm, Schleicher und Schüll) saturated in water and 2 freshly hatched larvae of the third larval stage are added. The larvae are placed next to the leaf discs. The experiment is incubated at 24° C. After 48 hours, an untreated savoy cabbage disc (10 mm Ø) is added. The feed behaviour and the state of the larvae are evaluated after 24, 48 and 72 hours. Per test concentration, 2 experiments and 3 repetitions are carried out. The insecticidal effect is stated as $LD_{100}$ (lethal dose for 100% of the larvae tested) after 72 hours.

| | Insecticidal activity against *Plutella xylostella* [µg/leaf disc] $LD_{100}$ |
|---|---|
| Omphalotin D | 100 |

EXAMPLE C

Effect of the Substance Omphalotin D According to the Invention on Insects

Test insect: *Phaedon cochleariae*

Test method: Using a cork borer, 2 discs having a diameter of 10 mm are punched out of savoy cabbage leaves and placed in a Petri dish (diameter 5.5 cm, Greiner). The test substance is pipetted onto the leaf discs and, after the solvent has evaporated, a filter disc (diameter 13 mm, Schleicher und Schull) saturated in water and 2 freshly hatched larvae of the third larval stage are added. The larvae are placed next to the leaf discs. The experiment is incubated at 24° C. After 48 hours, an untreated savoy cabbage disc (10 mm Ø) is added. The feed behaviour and the state of the larvae are evaluated after 24, 48, 72 and 96 hours. Per test concentration, 2 experiments and 3 repetitions are carried out. The insecticidal effect is stated as $LD_{100}$ (lethal dose for 100% of the larvae tested) after 96 hours.

| | Insecticidal activity against *Phaedon cochleariae* [µg/leaf disc] $LD_{100}$ |
|---|---|
| Omphalotin D | 100 |

EXAMPLE D

Effect of the Substances Omphalotin C and D According to the Invention on Insects Test Insect: *Spodoptera frugiperda*

Test method: A rectangle (1.5×2 cm) cut from maize leaves (8–10 day-old plant, variety Golda) is placed in a Petri dish (diameter 5.5 cm, Greiner). The test substance, as a methanolic solution, is applied to the maize leaf and, after the solvent has evaporated, a filter disc (diameter 13 mm, Schleicher und Schüll) saturated with water and a larva of the third larval stage are added. The larva is placed next to the piece of leaf. The experiment is incubated at 24° C. After 48 hours, untreated maize (1.5×2 cm) is added. The feed behaviour and the state of the larvae are evaluated after 24, 48 and 72 hours. Per test concentration, 4 experiments and 3 repetitions are carried out. The insecticidal effect is stated as $LD_{50}$ (lethal dose for 50% of larvae) after 72 hours.

| Insecticidal activity against *Spodoptera frugiperda* [μg/maize leaf] LD$_{50}$ | |
| --- | --- |
| Omphalotin C | 100 |
| Omphalotin D | 80 |

EXAMPLE E

Effect of the Substances Omphalotin B and C According to the Invention on Nematodes in the Greenhouse (Test Crop: Cucumbers)

Test nematode: *Meloidogyne incognita*

Test method: In each case two cucumber plants (variety Bella F1) are grown in a soil-leaf mixture in pots of the dimensions 7×7×6 cm. The test substances are, in the appropriate concentrations, dissolved in methanol and then diluted in water and then poured onto the cucumber plants, which are about 14 days old. Per drip, 10 ml of solution are poured on. 3 hours after the treatment, about 500 nematodes are pipetted as a suspension onto each pot. The pots are incubated in a greenhouse at a day temperature of about 26° C. and a night temperature of 20° C. After 14 days, evaluation is carried out by washing out the roots and determining the galls formed per plant.

The efficacy of the test substance is 100% if no galls have been formed, and it is 0% if the same number of galls have been formed as in the control.

| Variants | Fungus No. | ppm | Number of galls/plant | Efficacy in % |
| --- | --- | --- | --- | --- |
| 1 | Control | | 0 | |
| 2 | inf. control | | 103 | |
| 3 | inf. cont. with meth. | | 117 | |
| 4 | Omphalotin B | 5 | 0 | 100 |
| 5 | Omphalotin B | 2 | 1 | 99 |
| 6 | Omphalotin C | 5 | 0 | 100 |
| 7 | Omphalotin C | 2 | 1 | 99 |

EXAMPLE F

Effect of the Substances Omphalotin B–D According to the Invention on Insects Test insect: Hylemia antiqua

| Solvent: | 100 parts by weight of acetone |
| --- | --- |
| | 1900 parts by weight of methanol |

Test method: To produce a suitable extract preparation, 1 part by weight of extract is mixed with the stated amount of solvent, and the concentrate is diluted with methanol to the desired concentration. A stated amount of extract preparation of the desired concentration is pipetted onto a standardized amount of synthetic feed. After the methanol has evaporated, about 20 eggs of the onion fly (*Hylemia antiqua*) are placed onto the feed. After the desired period of time, the kill of the eggs and/or larvae in % is determined. 100% means that all animals have been killed; 0% means that none of the animals have been killed.

In this test, for example, the following compounds of the preparation examples have good activity:

| Extracts having the following active compound contents | Extract concentration in % | Kill in % after 7d |
| --- | --- | --- |
| Omphalotin B 55% Omphalotin C 29% Omphalotin D 12% | 0.0025 | 100 |
| Omphalotin B 7% Omphaiotin C 74% Omphalotin D 16% | 0.0025 | 100 |
| Omphalotin B 38% Omphalotin D 19% | 0.0025 | 100 |

EXAMPLE G

Effect of the Substances Omphalotin B–D According to the Invention on Mites

Test Mite: *Tetranychus urticae*

| Solvent: | 7.5 parts by weight of dimethylformamide |
| --- | --- |
| | 100 parts by weight of methanol |
| Emulsifier: | 2.5 parts by weight of alkylaryl polyglycol ether |

Test method: To produce a suitable extract preparation, 1 part by weight of extract is mixed with the stated amount of solvent and the stated amount of emulsifier, and the concentrate is diluted with emulsifier-containing water to the desired concentrations. Bean plants (*Phaseolus vulgaris*) which are heavily infested by all stages of the greenhouse red spider mite *Tetranychus urticae* are dipped into a preparation of active compound of the desired concentration. After the desired period of time, the effect in % is determined. 100% means that all spider mites have been killed; 0% means that none of the spider mites have been killed.

In this test, for example, the following compounds of the preparation examples show good activity:

| Extracts having the following active compound contents | Extract concentration in % | Kill in % after 6$^d$ |
| --- | --- | --- |
| Omphalotin B 55% Omphalotin C 29% Omphalotin D 12% | 0.05 | 60 |
| Omphalotin B 38% Omphalotin D 19% | 0.05 | 60 |
| Omphalotin C at least 95% | 0.05 | 70 |

EXAMPLE H

In vitro, omphalotin B exhibits, at a concentration of 1 μg/ml, a full effect against *Trichinella spiralis*. The test was carried out according to the test description in the publication Plant et al. (1996) Pesticide Science 48: 351–358.

In the in vivo mouse model, omphalotin B has full activity against the intestinal nematode Heterakis spumosa at a dosage of 50 mg/kg. The test is described in the above publication.

What is claimed is:

1. An omphalotin of the formula wherein $R^1$, $R^2$ and $R^3$ each independently represent hydrogen or acyl.

2. The omphalotin according to claim 1, wherein $R^1$, $R^2$ and $R^3$ each independently represent H, —CO—CH$_3$ or 3. A nematicidal, insecticidal and acaricidal composition comprising an omphalotin according to claim 1 and an extender.

4. A nematicidal, insecticidal and acaricidal composition comprising an omphalotin according to claim 1 and a surfactant.

5. An omphalotin produced by the fermentation of *Omphalotus olearis* strains having the following physico-chemical data and parameters:

|  | Omphalotin B | Omphalotin C | Omphalotin D |
|---|---|---|---|
| Appearance | white crystals | white crystals | white crystals |
| Melting Point | 180–183° C. | 173–178° C. | 165–170° C. |
| Empirical Formula | $C_{74}H_{123}O_{18}N_{13}$ | $C_{76}H_{125}O_{19}N_{13}$ | $C_{73}H_{119}O_{18}N_{13}$ |
| Molecular Weight | 1483 | 1525 | 1467 |
| Optical Rotation $[\alpha]D_{22}$(c2.0 in CH$_3$OH) | −246° | −242° | −254° | and spectra as set forth below:

$^1$H (500 MHz) NMR data (δ; multiplicity; J in Hz) for omphalotin B, C and D in CD$_3$OD, with the solvent signal (3.31 ppm) as reference:

| H | Omphalotin B | Omphalotin C | Omphalotin D |
|---|---|---|---|
| 1 | 6.95; d; 7.8 | 6.72/6.93; d; 7.9 | 6.72 16.93; d; 7.9 |
| 2 | 7.22; dd; 7.8, 8 | 7.22/7.17; dd; 8.8 | 7.22/7.17; dd; 8.8 |
| 3 | 6.87; dd; 7.5, 8 | 6.82/6.87; dd; 8.8 | 6.82/6.87; dd; 8.8 |
| 4 | 7.28; d; 7.5 | 7.26/7.28;d;7.5 | 7.26/7.28;d;7.5 |
| 7 | 5.53; s | 5.56/5.65; s | 5.56/5.65; s |
| 9a | 2.67; m | 2.66/2.48; m | 2.65/2.48; m |
| 9b | 2.52; m | 2.53/2.33; m | 2.52/2.32; m |
| 10 | 4.39; dd; 7.4; 8.6 | 4.42/5.15; m | 4.41/5.16; m |
| 12 | 2.70; s | 2.70/2.78; s | 2.70/2.78; s |
| 13 | 3.83; d; 10.8 | 4.41/3.89; d; 10.8 | 4.42/3.88; d; 10.8 |
| 14 | 2.30; m | 2.33/2.30; m | 2.32/2.29; m |
| 15 | 0.78; m | 0.77/0.82; m | 0.78/0.82; m |
| 16 | 0.78; m | 0.89/0.78; m | 0.89/0.78; m |
| 18 | 4.67; dd; 8.10 | 4.67/4.77; m | 4.68/4.78; m |
| 19 | 1.99; m | 1.99/2.07; m | 1.99/2.06; m |
| 20 | 0.84; m | 0.89/0.89; m | 0.87/0.90; m |
| 21a | 1.49; m | 1.47 1.46; m | 1.46/1.46; m |
| 21b | 1.35; m | 1.23/1.36; m | 1.22/1.37; m |
| 22 | 0.87; m | 0.88/0.87; m | 0.87/0.85; m |
| 24 | 3.17; s | 3.15/3.09; s | 3.15/3.09; s |
| 25 | 5.32; d; 10.8 | 5.29/5.23; d; 10.8 | 5.29/5.23; d; 10.8 |
| 26 | 2.27; m | 2.28 12.33; m | 2.29/2.33; m |
| 27 | 0.70; d; 6.8 | 0.68/0.73; d; 6.8 | 0.68/0.73; d; 6.8 |
| 28 | 0.89; m | 0.90/0.85; m | 0.93/0.85; m |
| 30 | 2.94; s | 2.91/2.94; s | 2.91/2.94; s |
| 31 | 5.30; d; 10.8 | 5.29/5.10; d; 10.8 | 5.28/5.08; d; 10.8 |
| 32 | 2.23; m | 2.25/2.31; m | 2.24/2.31; m |
| 33 | 0.74; m | 0.78/0.75; m | 0.77/0.75; m |
| 34 | 0.88; m | 0.90/0.93; m | 0.90/0.93; m |
| 36 | 3.12; s | 3.02/3.12; s | 3.02/3.12; s |
| 37a | 4.87; d; 16.5 | 4.90/4.84; d; 17 | 4.88/4.83; d; 17 |
| 37b | 3.68; d; 16.5 | 3.68/3.67; d; 17 | 3.67/3.65; d; 17 |
| 39 | 3.17; s | 3.17/3.16; s | 3.15/3.14; s |
| 40 | 5.11; s | 5.13/5.15; s | 5.12/5.13; s |
| 42 | 1.01; s | 1.02/1.21; s | 1.02/1.20; s |
| 43 | 1.20; s | 1.08/1.25; s | 1.08/1.25; s |
| 45 | 2.78; s | 2.83/2.76; s | 2.82/2.76; s |
| 46 | 5.20; d; 11 | 5.53/5.20; d; 10.9 | 5.55/5.22; d; 10.9 |
| 47 | 2.24; m | 2.25/2.28; m | 2.24/2.27; m |
| 48 | 1.10; d; 6.5 | 1.00/1.07; m | 0.99/1.05; m |
| 49 | 4.73; m | 4.68/4.69; m | 4.62/4.65; m |
| 50 | 1.30; d; 6.5 | 1.31/1.29; m | 1.30/1.28; |
| 52 | 2.67; s | 2.70/3.06; s | 2.70/3.06; s |
| 53 | 6.36; s | 7.01/7.23; s | 7.02/7.24; s |
| 55 | 4.79; m | 4.81/4.55; d; 7.8 | 4.81/4.55; d; 7.8 |
| 56 | 1.91; m | 2.00/2.08; m | 2.00/2.08; m |
| 57 | 0.74; m | 0.76/1.01; m | 0.76/1.01; m |
| 58 | 0.29; d; 6.5 | 0.32/0.96; d; 6.5 | 0.32/0.97; d; 6.5 |
| 60 | 3.10; s | 3.06/3.18; s | 3.06/3.18; s |
| 61 | 5.18; d; 11 | 5.43/5.16; d; 10.8 | 5.42/5.15; d; 10.8 |
| 62 | 2.18; m | 2.16/2.18; m | 2.16/2.18; m |
| 63 | 0.86; m | 0.85/1.02; m | 0.85/1.02; |
| 64a | 1.28; m | 1.25/1.07; m | 1.24/1.07; m |
| 64b | 1.28; m | 1.25/1.35; m | 1.24/1.35; m |
| 65 | 0.95; m | 0.86/0.83; m | 0.86/0.83; m |
| 67 | 2.83; s | 2.83/3.38; s | 2.82/3.38; s |
| 68a | 5.15; d; 17.3 | 5.05/5.14; d; 17 | 5.04/5.14; d; 17 |
| 68b | 4.25; d; 17.3 | 3.77/4.26; d; 17 | 3.77/4.25; d; 17 |
| 71 | 2.52; m | 2.52/2.52; m | 2.04/2.02; m |
| 73 | 1.32; s | 1.32/1.33; s |  |
| 74 | 1.32;s | 1.32/1.33; s |  |
| 76 | — | 2.17/2.27; s | 2.17/2.27; s |
| 17-NH | 8.17; d; 7.9 | 8.40; d; 9.0/8.18; d; 7.9 | 8.40; d; 9.0/8.18; d; 7.8 |

$^{13}$C (125 MHz) NMR data (δ; multiplicity) for omphalotin B, C and D in CD$_3$OD, with the signal (49.15 ppm) as reference:

| C | Omphalotin B | Omphalotin C | Omphalotin D |
|---|---|---|---|
| 1 | 113.4; d | 112.2/113.2; d | 112.2/113.2; d |
| 2 | 131.4; d | 131.2/131.4; d | 131.2/131.4; d |
| 3 | 121.2; d | 120.8/121.2; d | 120.8/121.2; d |
| 4 | 124.3; d | 124.01/24.3; d | 124.0/124.3; d |
| 5 | 131.5; s | 131.5/131.8; s | 131.5/131.8; s |
| 6 | 150.9; s | 150.0/150.8; s | 150.0/150.8;s |
| 7 | 83.3; d | 83.6/86.6; d | 83.6/86.6; d |
| 8 | 88.8; s | 88.9/90.2; s | 88.9/90.2; s |
| 9 | 41.6; t | 41.9/43.2; t | 41.9/43.2; t |
| 10 | 57.7; d | 57.9/58.3; d | 57.9/58.4; d |
| 11 | 174.7; s | 175.0/176.2; s | 175.0/176.2; s |
| 12 | 30.2; q | 30.2$^a$/30.3; q | 30.3$^d$/30.4; q |
| 13 | 67.9; d | 67.8/67.9; d | 67.9/67.9; d |
| 14 | 27.2; d | 27.2/27.4; d | 27.2/27.4; d |
| 15 | 19.8; q | 18.1/19.4; q | 18.1/19.4; q |
| 16 | 20.6; q | 20.1/20.5; q | 20.1/20.5; q |
| 17 | 169.8; s | 169.9/170.1; s | 169.9/170.1;s |
| 18 | 54.3; d | 54.4/54.6; d | 54.4/54.6; d |
| 19 | 35.9; d | 36.0/37.2; d | 36.0/37.2; d |
| 20 | 15.3; q | 15.7/16.3; q | 15.3/15.8; q |
| 21 | 26.4; t | 26.1/26.2; t | 26.1/26.2; t |
| 22 | 9.6; q | 9.8/11.4; q | 9.8/11.4; q |
| 23 | 174.7; s | 174.3/174.6; s | 174.3/174.6; s |
| 24 | 31.1; q | 30.9/31.1; q | 30.9/31.1; q |
| 25 | 59.6; d | 59.8/60.0; d | 59.8/60.0; d |
| 26 | 28.7; d | 28.4/28.6; d | 28.4/28.6; d |
| 27 | 19.1; q | 18.3/18.9; q | 18.3/18.9; q |
| 28 | 20.1; q | 19.8/20.3; q | 20.2/20.6; q |
| 29 | 172.4; s | 171.3/172.2; s | 171.3/172.2; s |
| 30 | 31.2; q | 31.0/31.3; q | 31.0/31.3; q |
| 31 | 58.8; d | 58.6/60.2; d | 58.8/60.2; d |
| 32 | 27.6; d | 27.6/27.8; d | 27.6/27.8; d |
| 33 | 18.3; q | 18.1/18.6; q | 18.1/18.6; q |
| 34 | 19.8; q | 19.8/20.7; q | 19.8/20.7; q |
| 35 | 172.8; s | 171.4/172.6; s | 171.4/172.6; s |
| 36 | 38.4; q | 37.6/38.3; q | 37.6/38.3; q |
| 37 | 51.3; t | 51.2/51.6; t | 51.2/51.6; t |
| 38 | 169.9; s | 170.0/170.4 | 170.0/170.4 |
| 39 | 33.2; q | 33.2/33.4; q | 33.3/33.4; q |
| 40 | 60.4; d | 59.3/60.3; d | 59.2/60.4; d |
| 41 | 75.5; s | 75.4/75.5; s | 75.3/75.5; s |
| 42 | 26.2; q | 26.1/26.2; q | 26.1/26.2; q |
| 43 | 29.2; q | 29.3/29.4; q | 29.3/29.4; q |
| 44 | 172.8; s | 172.9/173.2; s | 172.9/173.2; s |
| 45 | 31.7; q | 30.9$^b$/31.3; q | 30.9$^e$/31.3; q |
| 46 | 59.4; q | 55.6/58.8; d | 55.6/58.8; d |
| 47 | 37.6; d | 37.9/38.3; d | 37.6/37.9; d |
| 48 | 11.2; q | 10.4/11.2; q | 10.4/11.1; q |
| 49 | 70.4; d | 70.3/70.3; d | 70.4/70.4; d |
| 50 | 18.2; q | 17.9/18.2; q | 17.9/18.1; q |
| 51 | 170.8; s | 170.4/171.0; s | 170.6/171.1; s |
| 52 | 28.2; q | 29.4$^c$/31.0$^c$; q | 29.4$^d$/31.0$^f$; q |
| 53 | 77.0; d | 76.8/77.0; d | 76.9/77.0; d |
| 54 | 169.3; q | 166.6/167.4; s | 166.5/167.4; s |
| 55 | 56.1; d | 56.5/56.8; d | 56.5/56.7; d |
| 56 | 31.2; d | 30.9/31.9; d | 30.9/31.9; d |
| 57 | 18.7; q | 18.1/18.6; q | 18.1/18.6; q |
| 58 | 18.9; q | 19.1/19.7; q | 19.1/19.7; q |
| 59 | 174.6; s | 174.2/174.2; s | 174.1/174.2; s |
| 60 | 31.6; q | 31.4$^c$/31.5; q | 31.4$^f$/31.5; q |
| 61 | 59.0; d | 56.7/58.8; d | 56.8/59.2; d |
| 62 | 35.4; d | 34.4/35.1; d | 34.4/34.5; d |
| 63 | 16.4; q | 16.4/17.2; q | 16.4/17.2; q |
| 64 | 24.7; t | 25.8/25.8; t | 25.4/25.8; t |
| 65 | 11.4; q | 10.6/11.3; q | 10.6/11.3; q |
| 66 | 171.9; s | 171.9/173.2; s | 171.9/173.2; s |
| 67 | 35.1; q | 35.0$^b$/38.9; q | 35.1$^e$/38.9; q |
| 68 | 53.2; t | 51.7/53.2; t | 51.7/53.2; t |
| 69 | 170.2; s | 170.2/170.9; s | 170.2/170.9; s |
| 70 | 172.9; s | 172.6/173.2; s | 172.7/172.9; s |
| 71 | 49.1; t | 49.0/49.0; t | 21.5/21.6; q |
| 72 | 70.4; s | 70.3/70.4; s | — |
| 73 | 29.5; q | 29.6/29.6; q | — |
| 74 | 29.6; q | 29.6/29.6; q | — |
| 75 | — | 170.3/170.6; s | 170.3/170.6; s |
| 76 | — | 20.4/20.6; q | 20.5/20.7; q |

$^{a, b, c, d, e, f}$exchangeable.

6. An omphalotin having the formula wherein $R^1$, $R^2$ and $R^3$ each independently represent hydrogen or acyl, wherein said omphalotin is selected from the group consisting of omphalotins having the following physicochemical parameters:

| | Omphalotin B | Omphalotin C | Omphalotin D |
|---|---|---|---|
| Melting Point | 180–183° C. | 173–178° C. | 165–170° C. |
| Empirical Formula | $C_{74}H_{123}O_{18}N_{13}$ | $C_{76}H_{125}O_{19}N_{13}$ | $C_{73}H_{119}O_{18}N_{13}$. |

7. A process for preparing a composition comprising mixing an extender or a surfactant with an omphalotin according to claim 1 in an amount effective to inhibit growth of insects, arachnids or nematodes; and recovering the composition.

8. A process for preparing an omphalotin according to claim 1 comprising the steps of:
 (a) cultivating a fungus of the genus Omphalotus or Lampteromyces in a culture medium for a time and under aerobic conditions effective to form an omphalotin according to claim 1, and
 (b) isolating the omphalotin according to claim 1,
wherein said culture medium contains mineral salts as well as an assimilable carbon and nitrogen source.

9. The process of claim 8 wherein the fungus is of the Omphalotus genus.

10. The process of claim 8 wherein the fungus is a strain of *Omphalotus olearius*.

11. The process of claim 10 wherein the fungus is a strain of *Omphalotus olearius* selected from the group consisting of number 83039, 90173, 91050, 92095, 93162 and 90170.

12. A method of inhibiting growth of a pest selected from the group consisting of insects, arachnids and nematodes comprising contacting the pest with an omphalotin according to claim 1 for a time and under conditions effective to inhibit the growth of the pest.

13. A method for reducing the number or viability of arthropods and/or nematodes present in an in vitro space, comprising the step of applying an omphalotin according to claim 1 to arthropods, nematodes or to a habitat of said arthropods or nematodes for a time and under conditions effective to reduce the number or viability of said arthropods and/or nematodes.

14. A method of inhibiting growth of pathogenic endoparasites, comprising administering an omphalotin of claim 1 to an animal in need thereof for a time and under conditions effective to inhibit growth of said pathogenic endoparasites.

15. A method according to claim 14, wherein said animal is a warm-blooded animal.

16. A method according to claim 15, wherein the warm-blooded animal is selected from humans, non-human mammals, and birds.

17. The method of claim 14, wherein the pathogenic endoparasites inhabit the body of a human, an animal or an insect and are selected from the group consisting of cestodes, trematodes, nematodes and acantocephalans;

wherein said animal is selected from the group consisting of a cow, a horse, a sheep, a pig, a goat, a camel, a water buffalo, a donkey, a rabbit, a fallow deer, a reindeer, a mink, a chinchilla, a raccoon, a mouse, a rat, a guinea pig, a golden hamster, a dog, a cat, a chicken, a goose, a turkey, a duck, a fresh-water fish, a salt-water fish, and a reptile; and wherein said insect is selected from the group consisting of a honey bee and a silkworm.

18. The method of claim 14 wherein said pathogenic endoparasites comprise pathogenic nematodes.

19. The method of claim 14 wherein the pathogenic endoparasites are selected from cestodes, trematodes, nematodes, acantocephalans and combinations thereof.

* * * * *